(12) United States Patent
Bertling

(10) Patent No.: US 6,383,802 B1
(45) Date of Patent: May 7, 2002

(54) METHOD AND DEVICE FOR PREPARING SAMPLES FOR DETECTING A NUCLEOTIDE SEQUENCE

(75) Inventor: Wolf Bertling, Erlangen (DE)

(73) Assignee: November Aktiengesellschaft Gesellschaft fur Molekulare Medizin, Erlangen (DE)

( * ) Notice: Subject to any disclaimer, the term of this patent is extended or adjusted under 35 U.S.C. 154(b) by 0 days.

(21) Appl. No.: 09/719,376

(22) PCT Filed: May 29, 1999

(86) PCT No.: PCT/DE99/01589

§ 371 Date: Dec. 11, 2000

§ 102(e) Date: Dec. 11, 2000

(87) PCT Pub. No.: WO99/64157

PCT Pub. Date: Dec. 16, 1999

(30) Foreign Application Priority Data

Jun. 12, 1998 (DE) .......................................... 198 26 153

(51) Int. Cl.[7] .............................. C12M 3/00; C12Q 1/68; C07H 21/04
(52) U.S. Cl. ................................. 435/287.2; 435/287.2; 435/6; 435/91.1; 435/91.2; 536/23.1; 536/24.3; 536/24.33
(58) Field of Search ..................... 435/287.2, 6, 91.1, 435/91.2, 183; 536/23.1, 24.3, 24.33

(56) References Cited

U.S. PATENT DOCUMENTS

| | | |
|---|---|---|
| 5,484,734 A | 1/1996 | Kimura |
| 5,556,773 A | 9/1996 | Yourno |
| 5,585,242 A | 12/1996 | Bouma et al. |
| 5,604,130 A | 2/1997 | Warner et al. |

FOREIGN PATENT DOCUMENTS

| | | |
|---|---|---|
| FR | 2 672 301 A1 | 8/1992 |
| GB | 2 333 250 A | 7/1999 |

OTHER PUBLICATIONS

WO 98/25701, Publication Date: Jun 18, 1998, Microfabricated Sleeve Devices for Chemical Reactions.
WO 96/02836, Publication Date: Feb. 1, 1996, Automatic Processing System for Use in Solid Phase Biospecific Binding and DNA Sequencing.

*Primary Examiner*—B. L. Sisson
(74) *Attorney, Agent, or Firm*—Rankin, Hill, Porter & Clark LLP

(57) ABSTRACT

The invention relates to a method for preparing samples for detecting a nucleotide sequence by polymerase chain reaction (PCR), according to which a) an analysis solution is filled into at least one cavity (2) provided for in a support (1); b) a lid (3) configured complementary to the shape of the cavity (2) is placed onto the support (1) in such a way that the analysis solution is pushed at least partly into a gap (S) formed between the cavity (2) and the lid (3); and c) the gap (S) is sealed by means of at least one seal (5, 12) provided for near an opening in the cavity (2).

31 Claims, 3 Drawing Sheets

METHOD AND DEVICE FOR PREPARING SAMPLES FOR DETECTING A NUCLEOTIDE SEQUENCE

FIELD OF THE INVENTION

The present invention generally relates to a method for preparing samples for detecting a nucleotide sequence by means of polymerase chain reaction.

DESCRIPTION OF RELATED ART

U.S. Pat. No. 5,455,175 discloses a so-called thermocycler with which a plurality of liquid biological samples can be exposed repeatedly to a pre-set temperature profile in order to carry out the PCR. To shorten the time required for the temperature treatment, a small volume of each of the biological samples is taken up in a thin-walled glass capillary. To this end, each of the individual samples must be filled into the capillary and then sealed in. This is time-consuming.

DE 33 36 738 A1 discloses a titer plate, a lid of which can only be removed from the support with the expenditure of considerable force. A sample taken up in the known device is difficult to heat externally; the device is unsuitable for carrying out the PCR.

SUMMARY OF THE INVENTION

It is an object of the present invention to overcome the disadvantages of the prior art. In particular, it is intended to provide a method and a device with which the time required for preparing the samples for PCR is reduced. A further aim of the invention is a simplified and improved, in particular real-time, detection and an increase in sensitivity.

In accordance with the invention, there is provided a method for preparing samples for detecting a nucleotide sequence by means of polymerase chain reaction, where a) an analysis solution is filled into at least one cavity provided on a support, b) a lid configured complementary to the shape of the cavity is placed onto the support in such a way that at least some of the analysis solution is displaced into a gap formed between the cavity and the lid and c) the gap is sealed by means of at least one seal provided near an opening of the cavity.

The proposed process considerably shortens the time for sample preparation. The procedure of sealing the sample solution into a capillary is dispensed with.

The analysis solution can have added to it a first and/or a second primer. It is regarded as particularly advantageous to have a third primer, preferably with its 5'-terminal end, bound to the internal face of the lid which extends into the cavity. In this manner, it is possible to bind, to the third primer, a nucleotide sequence which may be present in a sample. This can be achieved in a particularly simple fashion by immersing the internal face of the lid into the sample. After the amplification cycles have been concluded, it is furthermore possible to accumulate the amplified nucleic acid on the internal face by binding it to the third primer. The accumulation is expediently carried out by applying an electric field. The nucleotide sequence is shifted toward the third primer under the influence of an electrical field.

To detect the presence of the nucleotide sequence of interest, it is expedient to examine the analysis solution and/or one of the primers for their fluorescence properties. Upon binding of the nucleotide sequence to be detected to one of the primers, a change in the fluorogenic properties of the substances present in the analysis solution may, take place. Upon binding of the nucleotide sequence to be detected to one of the primers, a spatial relationship between two fluorophoric groups is preferably alterable in such a way that a fluorescence reaction can be generated, altered or quenched.

In a further embodiment, the analysis solution is heated and cooled cyclically. A typical temperature cycle consists of a first heating of the analysis solution to 90 to 92° C., a cooling to 50 to 55° C. and a second heating to 72 to 75° C. During the first heating, denaturation takes place, during the cooling, renaturation, and during the second heating the synthesis of the nucleotide sequence. The abovementioned cycle is repeated approximately 30 times.

Heating can be effected by means of light, preferably infra-red radiation, resistance heating or by passing of gas or a fluid around the cavity. Rapid cooling is effected expediently by passing a gas, for example air, or a fluid around the cavity, or by means of a Peltier element.

Furthermore provided in accordance with the invention is a device for detecting a nucleotide sequence which may be present in a sample by means of polymerase chain reaction, where the cavity has a surrounding lateral wall which widens conically toward the opening and the gap has a width of not more than 1 mm.

The proposed device allows time-saving sample preparation. By using it, the time required for carrying out a PCR can be reduced considerably. The lid can be lifted without great expenditure of force after the PCR has been carried out.

It is advantageous to provide a facility for cyclically heating and cooling the analysis solution. Moreover, a facility for examining the fluorescence properties of the analysis solution and/or one of the primers may be provided.

The support can be made of a translucent material, preferably of glass or plastic. The cavity is expediently designed to have planar sections; preferably, it has a flat bottom. On the support and/or on the internal face of the lid, a further seal may be provided at sections located between the cavities or on projections arranged on the internal face of the lid. Like the seal, the further seal can be made of, for example, rubber, silicone, Teflon or other suitable materials.

It is considered to be especially advantageous for the support to have 96 cavities and for the lid 96 projections which are complementary to the shape of the cavities. Thus, for example the support can have approximately the dimension of a conventional 96-well microtiter plate. Naturally, the support may also have a fraction or a multiple of the abovementioned number of cavities.

In accordance with a further embodiment, the lid can be made of an electricroconductive material, preferably a plastic. The support can exhibit an electrode, preferably an electrode made of platinum, so that an electrical field can be applied between the lid and the support, by which nucleotide sequence present in the analysis solution can be shifted to the internal face and accumulated by field-inversion cycles.

The plastic can comprise a polycarbonate, a trimenthylthiophene, triaminobenzene and/or a polycarbene, and at least sections of the internal face of the lid can be provided with a substance which binds biomolecules. Binding of the nucleotide sequence to the plastic can be mediated here by streptavidin or avidin.

The analysis solution advantageously has a first and/or second primer added to it. It is considered as especially advantageous for a third primer to be bound to the internal face of the lid facing the cavity, preferably with a 5'-terminal end. This allows the amplified nucleotide sequence to be removed from the analysis solution.

In accordance with a further embodiment, a means for exciting fluorescence between the bottom and the internal face of the lid is provided. It is possible that the radiation originating from the excitation means can be focused toward the internal face of the lid. This is advantageous in particular when the nucleotide sequence is bound to the internal face via the third primer. The means for exciting fluorescence is expediently generated by a laser diode. Thus, it takes the form in this instance of laser light. Excitation of the support bottom can also be achieved by a so-called gally-mode laser (Science 1998, 280, p 1501, 1544 ff.) in a pre-set manner, either simultaneously or successively.

There may furthermore be provided a facility for detecting the fluorescence, a facility for evaluating the fluorescence observed, and a facility for shifting the support relative to the means for exciting the fluorescence and/or to the detection facility. Moreover, there may be provided a facet-eye-like means for separately exciting and/or detecting the fluorescence between each bottom and the internal face of the corresponding lid. This saves yet more analysis time.

Expediently, at least sections of the lid and/or the support are black so that heat radiated at them is absorbed in an efficient manner. In particular, they are composed of a highly thermoconducting material.

There may furthermore be provided a facility for cyclically heating and cooling the analysis solution, it being advantageous to provide, for heating, a means for generating light, preferably infra-red radiation, a resistance heating or a means for passing a gas or a fluid around the cavity. It is furthermore expedient to provide a means for cooling, the cooling preferably being achieved by passing a gas or a fluid around the cavity, or by means of a Peltier element.

To improve the thermoconductivity while simultaneously having good transparency properties, the support can have a bottom made of glass. The seal is expediently formed by a recess surrounding the lateral wall, which is preferably made of plastic, and a surrounding reinforcement which is provided at the projection so that it complements the recess and which can lock positively into the recess. The seal is expediently self-sealing when the pressure in the cavity rises, for example owing to an increase in temperature, by pressing the reinforcement against the recess. The lid can be put on or taken off in a particularly simple fashion by gently bending it, owing to a high flexibility of the sections between the projections.

Finally, there is claimed a kit for carrying out the method according to the invention, with
a) a support with at least one cavity and
b) a lid configured complementary to the cavity which can be placed onto the support in such a way that at least some of the analysis solution taken up by the cavity can be displaced into a gap formed between the cavity and the lid and
c) an analysis solution comprising at least one first primer.

The analysis solution can comprise a second primer. A third primer can be bound to an internal face of the lid facing the cavity, preferably with its 5'-terminal end.

BRIEF DESCRIPTION OF THE DRAWINGS

These and further features of the invention are apparent with reference to the following description and drawings, wherein.

DETAILED DESCRIPTION OF THE PREFERRED EMBODIMENTS

Figure 1:
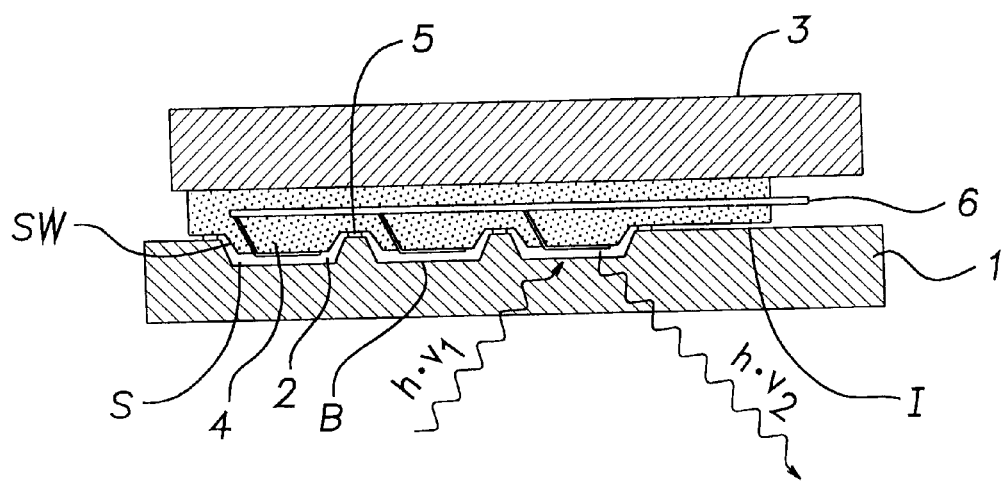
FIG. 1 shows a schematic cross-sectional view through a first device.
Figure 2:
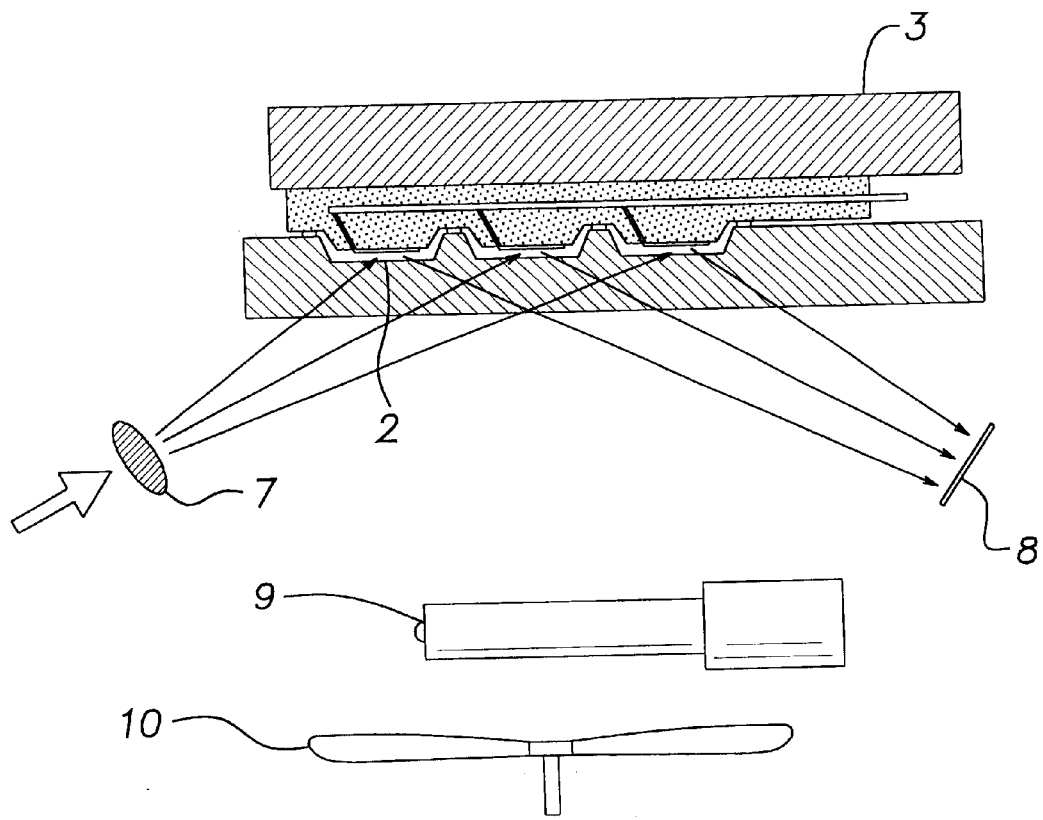
FIG. 2 the device of FIG. 1 upon excitation and detection.

In FIG. 1, a support 1 has several cavities 2. A lid 3 is provided on its internal face I with a plurality of projections 4. The projections 4 have a shape which is complementary to the cavity 2. Between a bottom B of the cavity 2 and the opposite projection 4 which runs in parallel a gap G is formed. The cavity 2 is furthermore delimited by a surrounding lateral wall LW which opens out conically from the bottom B to the opening of the cavity 2. The gap G formed between the projection 4 and the cavity 2 has a width of not more than 1 mm. A seal 5 is provided in the vicinity of the opening of the cavity 2. 6 denotes an electrode integrally molded into the lid 3. The electrode 6 includes a series of electrode portions, each of which overlie one of the cavities 2, as illustrated. The support 1 can have a counterelectrode (not shown) that cooperates with the electrode portions so that an electrical field can be applied between the lid and the support, by which nucleotide sequence present in the analysis solution can be shifted to the internal face and accumulated by field-inversion cycles FIG. 2 shows the device of FIG. 1 upon excitation and detection. 7 schematically designates an optical facility for exciting the analysis solution taken up by the gap G. It takes the form of a facet-eye-like means by means of which a plurality or all of the cavities 2 can simultaneously receive, for example, laser light. The optical facility 7 is focused at the internal face I, of the lid 3, which is arranged opposite of the bottom B. 8 designates a fluorometer. The fluorometer 8, too, can be provided with a facet-eye-like means so that the fluorescence emanating from a plurality or all of the cavities 2 can be detected. An infra-red radiation source 9 and a fan 10 are located opposite the support 1.

Figure 3:
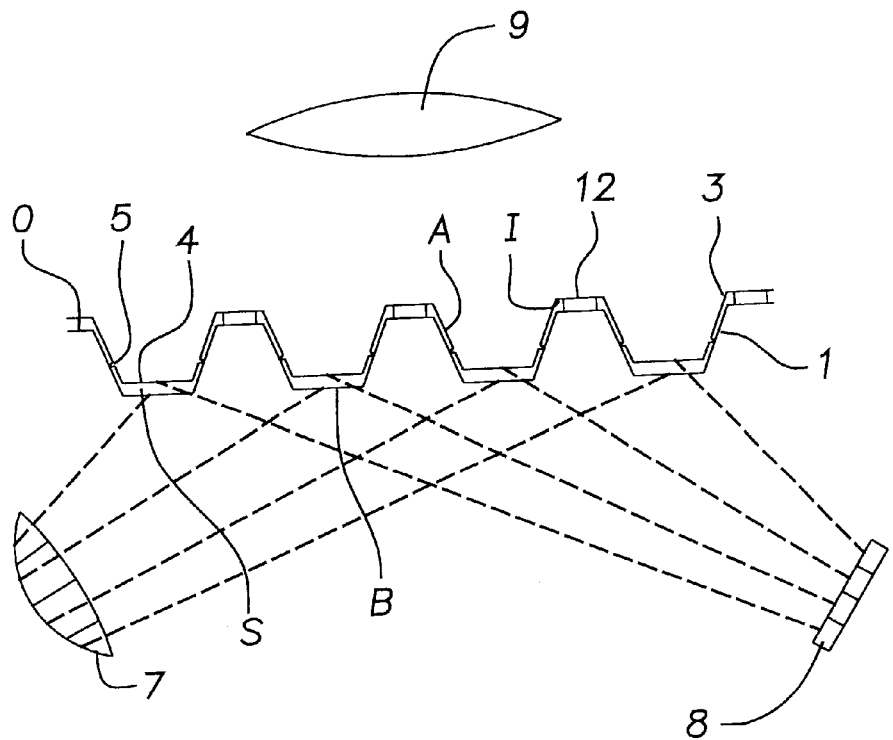
FIG. 3 a schematic cross-sectional view of a second device upon excitation and detection, FIG. 3a a schematic cross-sectional view of the device of FIG. 3, FIG. 4 a schematic partial cross-sectional view of a third device, FIG. 5 a schematic cross-sectional view of a seal and FIG. 6 the cross-sectional view of FIG. 5 in the unlocked state.
Figure 3A:
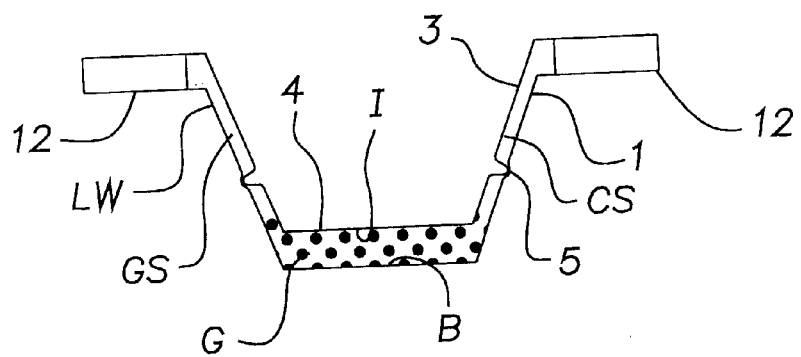

FIGS. 3 and 3a show a schematic cross-section through a second device. Here, the infra-red radiation source 9 is arranged opposite the lid 3. The lid 3 is made of a black, highly thermoconductive material, for example a glass or metal. For better absorption, the external face A of the lid 3, which is opposite the internal face I, is coated with a black paint. The first seal 5 is designed as a self-sealing locking connection. A second seal 12 in the vicinity of the edge of the opening of the cavity 2 is composed of rubber or elastomer. It is provided between the internal face I of the lid 3 and an upper face U of the support 1. When the lid 3 is shut, an analysis solution taken up by the cavity 2 is displaced into a gap segment GS located between the lateral wall LW and a facing curved surface CS of the projection 4.

Figure 4:
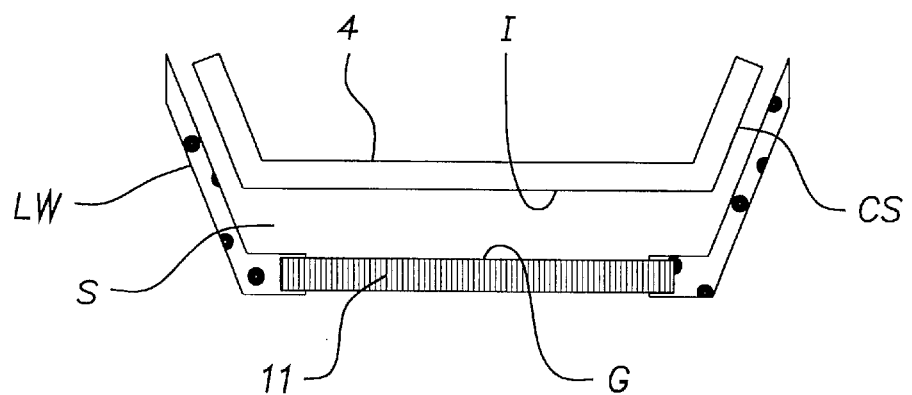

In FIG. 4, too, the support 1 is configured complementary to the lid 3. Again, it is made of a highly thermoconductive material. The bottom B is made of a transparent material, for example a glass window 11.

Figure 5:
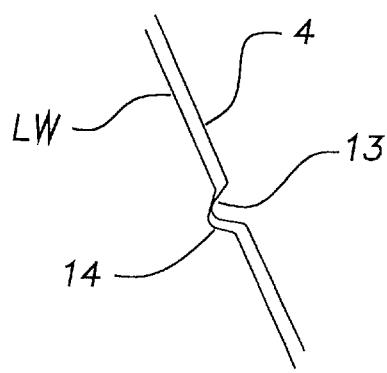
Figure 6:
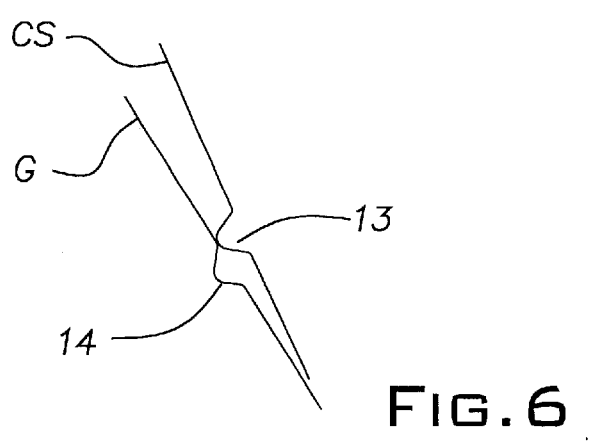

FIG. 5 shows a schematic partial cross-sectional view through the first seal 5. Here, a surrounding reinforcement 13 provided at the curved surface CS of the projection 4 engages, in the closed state, positively and nonpositively into a surrounding recess 14 provided at the lateral wall LW. FIG. 6 shows the first seal 5 in the as yet nonpositively locked state.

The device has the following function:

To prepare the samples, analysis solution is pipetted into the cavity 2 of the support 1. Pipetting can be carried out for example with the aid of an automatic pipette. The analysis solution preferably takes the shape of a so-called master mix in which all the agents required for carrying out the PCR are present. In particular, a first and a second primer are present in the analysis solution. A third primer is bound to the internal face I of the lid 3 in the region of the projections 4. The nucleotide sequence to be detected is bound to the third primer. Binding can take place for example by previously dipping the lid 3 into a sample solution in which the nucleotide sequence to be detected is present.

To prepare the samples, the lid 3 now only needs to be placed onto the support 1 in such a way that the projections 4 are immersed into the complementary cavities 2. During this process, the third primer with the nucleotide sequence bound to it comes into contact with the analysis solution. The lid 3 is closed with the support 1 so that a seal is formed, for example by the reinforcements 13 provided at the projections 4 locking into the complementary recesses 14 of the cavities 2. In this state, some of the analysis solution is displaced into the gap G.

Then, in particular the gap G formed between the internal face I and the bottom B is subjected to the temperature treatment required for carrying out the PCR. Thereupon, or else between each temperature cycle, the region located between internal face I and bottom B of each cavity 2 is excited by means of the optical facility 7 and then tested for fluorescence using the fluorometer 8. A change in fluorescence indicates the presence or absence of the nucleotide sequence of interest.

The temperature cycles are caused by repeatedly activating or deactivating the IR radiation source 9 or the fan 10.

What is claimed is:

1. A device for preparing one or more samples for detecting a nucleotide sequence by means of polymerase chain reaction (PCR) where each sample is contacted with an analysis solution, said device comprising a support (1) with at least one cavity (2), a lid (3) which is configured complementary to the cavity (2) and which can be placed on the support (1) such that at least some of the analysis solution taken up by the cavity (2) can be displaced into a gap (2) formed between the cavity (2) and the lid (3) and with a seal (5, 12), arranged adjacent an opening of the cavity (2) for sealing the gap (G), wherein the cavity (2) has a surrounding lateral wall (LW) which widens conically toward the opening and the gap (G) has a width (W) of not more than 1 mm, an electrode (6) being integrally molded into the lid (3) and a primer being bound to an internal face (I) of the lid (3), which faces the cavity (2).

2. The device according to claim 1, further comprising a facility for cyclically heating and cooling the analysis solution.

3. The device according to claim 1, further comprising a facility for examining the fluorescence properties of at least one of the analysis solution and one of the primers.

4. The device according to claim 1, wherein the support is made of a translucent material.

5. The device according to claim 1, wherein the cavity has planar sections and has a flat bottom (B).

6. The device according to claim 5, further comprising means for exciting fluorescence between the bottom (B) and the internal face (I) of the lid (3).

7. The device according to claim 6, wherein radiation originating from the excitation means can be focused toward the internal face (I) of the lid (3).

8. The device according to claim 6, wherein the means (7) for exciting fluorescence is generated by a laser diode.

9. The device according to claim 6, further comprising a facility (8) for detecting the fluorescence.

10. The device according to claim 9, further comprising a facility for evaluating the detected fluorescence.

11. The device according to claim 9, further comprising a facility for shifting the support (1) relative to at least one of the means (7) for exciting the fluorescence and the detection facility (8).

12. The device according to claim 11, further comprising a facet-eye-like means for separately exciting and/or detecting the fluorescence between each bottom (B) and the internal face (I) of the corresponding lid (3).

13. The device according to claim 1, comprising a further seal (12), said further seal being provided on the support (1) and/or on the internal face (I) of the lid (3) in sections located between the cavities (2) or on projections (4) provided on the internal face (I) of the lid (3).

14. The device according to claim 1, wherein the support has 96 cavities (2) and the lid (3) 96 projections (4), said projections being complementary to the shape of the cavities (2).

15. The device according to claim 1, wherein the lid (3) is made of an electroconductive plastic material.

16. The device according to claim 15, wherein the plastic material is selected from the group consisting of polycarbonate, trimethylthiophene, triaminobenzene and polycarbene and at least sections of the internal face (I) of the lid (3) are provided with a substance which binds biomolecules.

17. The device according to claim 11, wherein the support (1) has a counterelectrode that is operatively linked with the lid electrode (6) so that an electrical field can be applied by means of which nucleotide sequence present in the analysis solution can be shifted to the internal face (I) and accumulated by field-inversion cycles.

18. The device according to claim 17, wherein a portion of said electrode (6) is exposed at said face (I) of said lid (3).

19. The device according to claim 11, wherein the analysis solution has a first primer added to it.

20. The device according to claim 19, wherein the analysis solution has a second primer added to it.

21. The device according to claim 11, wherein said primer is bound to the internal face (I) of the lid (3) facing the cavity (2), with its 5'-terminal end.

22. The device according to claim 11, wherein at least sections of the lid (3) and/or the support (1) are black so that heat radiated at them is absorbed in an efficient manner.

23. The device according to claim 22, further comprising a facility for cyclically heating and cooling the analysis solution.

24. The device according to claim 23, further comprising a heating means (9), said heating means being selected from the group consisting of infra-red radiation heaters, resistance heating and means for passing a gas or a fluid around the cavity (2).

25. The device according to claim 23, further comprising means (10) for cooling, preferably by passing a gas or a fluid around the cavity (2), or by means of a Peltier element is provided.

26. The device according to claim 25, wherein the support (1) has a bottom (B) made of glass.

27. The device according to claim 11, wherein the seal (5) is formed by a recess 14 surrounding the lateral wall (LW) and a surrounding reinforcement (13), which is provided at the projection 4 so that it complements the recess (14) and can lock positively into the recess (14).

28. The device according to claim 27, wherein, when pressure in the cavity (2) rises, the seal (5) is self-sealing by pressing the reinforcement (13) against the recess (14).

29. A kit for preparing samples for detecting a nucleotide sequence by means of polymerase chain reaction (PCR) where the sample is contacted with an analysis solution, said kit comprising:

a) a support (1) with at least one cavity (2), b) a lid (3) configured complementary to the cavity (2), said lid being placed onto the support (1) such that at least some of the analysis solution taken up by the cavity (2) can be displaced into a gap (G) formed between the cavity (2) and the lid (3), said lid having an electrode (6) integrally molded therein, and c) an analysis solution comprising at least one first primer.

30. The kit according to claim 29, further comprising a second primer in the analysis solution.

31. The kit according to claim 30, wherein a third primer is bound to an internal face (I) of the lid (3) facing the cavity (2), preferably with its 5'terminal end.

* * * * *

UNITED STATES PATENT AND TRADEMARK OFFICE
CERTIFICATE OF CORRECTION

PATENT NO.   : 6,383,802 B1                                          Page 1 of 1
DATED        : May 7, 2002
INVENTOR(S)  : Bertling It is certified that error appears in the above-identified patent and that said Letters Patent is hereby corrected as shown below:

<u>Title page, Item [54] and Column 1, line 1,</u>
Title, delete "METHOD AND".

<u>Column 1,</u>
Line 3, insert "BACKGROUND OF THE INVENTION".
Line 6, delete "method" and insert -- device --.

<u>Column 6,</u>
Line 31, delete "claim 11" and insert -- claim 1 --.
Line 39, delete "claim 11" and insert -- claim 1 --.
Line 43, delete "claim 11" and insert -- claim 1 --.
Line 46, delete "claim 11" and insert -- claim 1 --.
Line 63, delete "claim 11" and insert -- claim 1 --.

Signed and Sealed this

First Day of October, 2002

*Attest:*

*Attesting Officer*

JAMES E. ROGAN
*Director of the United States Patent and Trademark Office*